US00PP17101P3

(12) United States Plant Patent
Trees

(10) Patent No.: US PP17,101 P3
(45) Date of Patent: Sep. 19, 2006

(54) ***VERBENA* PLANT NAMED 'BALAZWILRO'**

(50) Latin Name: *Vebena hybrida*
Varietal Denomination: Balazwilro

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 185 days.

(21) Appl. No.: 11/011,419

(22) Filed: Dec. 13, 2004

(65) Prior Publication Data

US 2006/0130203 P1 Jun. 15, 2006

(51) Int. Cl.
*A01H 5/00* (2006.01)

(52) U.S. Cl. ..... Plt./308

(58) Field of Classification Search ..... Plt./308
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of *Verbena* plant named 'Balazwilro' characterized by its rose pink-colored flowers with "eye", dark green-colored foliage, good basal branching character, and spreading and trailing growth habit.

1 Drawing Sheet

Latin name of genus and species of plant claimed: *Verbena hybrida.*
Variety denomination: 'Balazwilro'.

BACKGROUND OF THE INVENTION

The present invention comprises a new and distinct *verbena* plant botanically known as *Verbena hybrida* and hereinafter referred to by the cultivar name 'Balazwilro'.

The new cultivar was developed by the inventor through a controlled breeding program during December 2001 at Arroyo Grande, Calif. The objective of the breeding program was the development of *verbena* cultivars with trailing habit, continuous flowering, excellent basal branching, small, dark green-colored foliage, and unique flower coloration.

The female (seed) parent of the new cultivar was the proprietary *Verbena* breeding selection designated BFP-0970, not patented, which exhibits a semi-trailing habit, bright red-colored flowers, and dark green-colored foliage. The male (pollen) parent of the new cultivar was the proprietary *Verbena* breeding selection designated BFP-1476, not patented, which exhibits a semi-trailing habit, bright red-colored flowers with 'eye' and dark green-colored foliage.

The new cultivar was discovered and selected by the inventor as a single plant within the progeny of the above stated cross-pollination in April 2002.

Asexual reproduction of the new cultivar by terminal cuttings since April 2002 has demonstrated that the characteristics of the new cultivar, as herein described, reproduce true to type and are firmly fixed and retained through successive generations of such asexual propagation.

SUMMARY OF THE INVENTION

The following characteristics of the new cultivar have been repeatedly observed and can be used to distinguish 'Balazwilro' as a new and distinct cultivar of *Verbena* plant:

1. Rose pink-colored flowers with "eye".
2. Lobed, dark green-colored foliage.

3. Good basal branching character.
4. Spreading and trailing growth habit.

Plants of the new cultivar differ from plants of the female parent primarily in flower color and from the male parent primarily in flower color.

Plants of the new cultivar are most similar to the cultivar 'Lan Bright Pink', U.S. Plant Pat. No. 13,982. However, in side-by-side comparison, plants of the new cultivar differ from plants of 'Lan Bright Pink' in the following characteristics:

1. The flowers of the new cultivar are a darker pink-color than the flowers of 'Lan Bright Pink'.
2. the leaves of the new cultivar are brighter and less yellow than the leaves of 'Lan Bright Pink'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from color values sited in the detailed description, which more accurately describes the colors of 'Balazwilro'. The plants were grown in 10 cm pots for 13 weeks in a greenhouse at West Chicago, Ill.

DETAILED BOTANICAL DESCRIPTION

Figure 1:
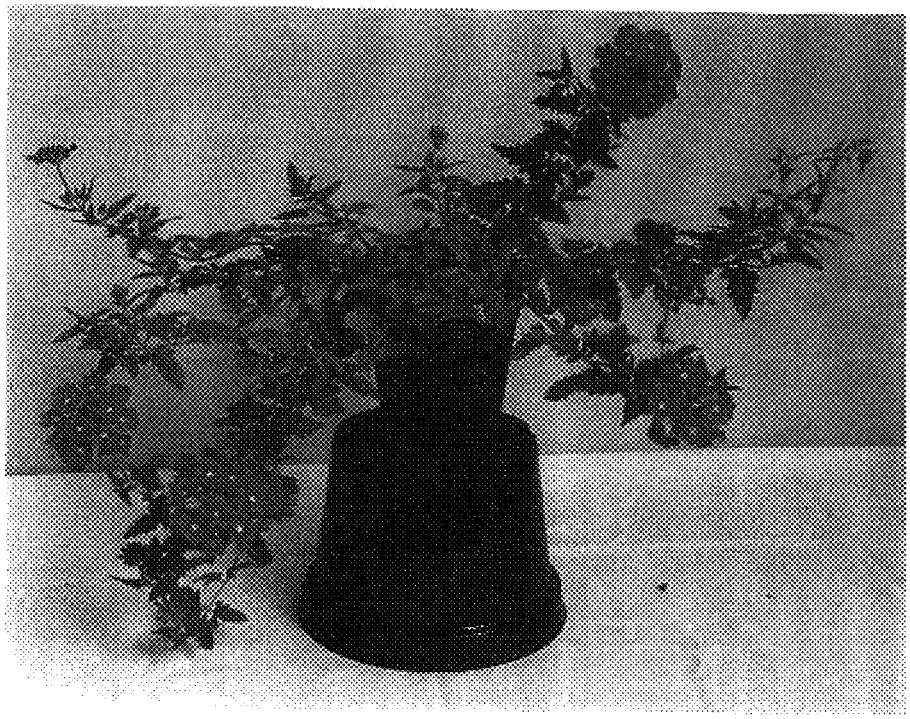
FIG. 1 illustrates a side view of the overall growth and flowering habit of 'Balazwilro'.
Figure 2:
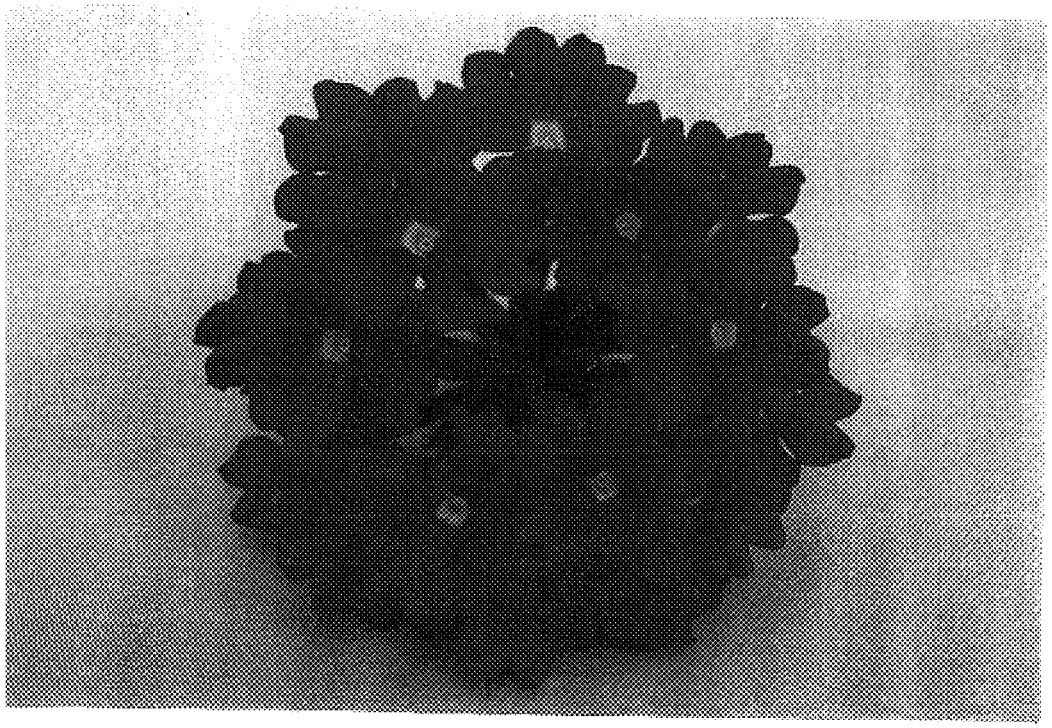
FIG. 2 illustrates a close-up view of an individual inflorescence of 'Balazwilro'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition except where color terms of ordinary significance are used. The color values were determined on Sep. 24, 2004. The readings were taken between 11:00 and 11:30 a.m. under natural light conditions.

The following description and measurements describe plants produced from cuttings taken from stock plants and grown in a double polycarbonate-covered greenhouse under conditions comparable to those used in commercial practice. The plants were grown at West Chicago, Ill. in 10 cm pots for 13 weeks utilizing a soil-less growth medium. Greenhouse temperatures were maintained at approximately 70–80° F. (21–26° C.) during the day and approximately 62–65° F. (17–18° C.) during the night. Greenhouse light levels were maintained at approximately 5,000–8,000 foot-candles during the day.

Botanical classification: *Verbena hybrida* cultivar Balazwilro.

Parentage:

*Female parent.*—Proprietary *verbena* breeding selection BFP-0970, not patented.

*Male parent.*—Proprietary *verbena* breeding selection BFP-1476, not patented.

Propagation:

*Type cutting.*—Terminal tip.

*Time to initiate roots.*—Approximately 6–9 days.

*Time to produce a rooted cutting.*—Approximately 21–28 days.

*Rooting habit.*—Freely branching.

*Rooting description.*—Fibrous.

Plant description:

*Crop time.*—Approximately 5–7 weeks from a rooted cutting to finished flowering plant.

*Growth habit.*—Moderately vigorous with good basal branching. Pinching improves basal branching.

*Form.*—Spreading and trailing.

*Size.*—Height from soil level to top of plant plane: Approximately11.6 cm. Width (area of spread): Approximately 53.6 cm.

*Branch.*—Quantity: Approximately 7 per plant. Shape: Square in cross section. Length from soil level to base of peduncle: Approximately 22 cm. Diameter: Approximately 2.2 mm. Texture: Densely pubescent with short soft hairs. Color: 144A with some overlay of 183C especially along all four edges. Length of internode at middle of branch: Approximately 2.1 cm.

*Foliage.*—Type: Simple. Fragrance: None. Arrangement: Opposite. Orientation to stem: Right Angle. Shape: Ovate. Margin: Lobed. Apex: Acute. Base: Truncate. Texture of upper surface: Densely covered with short stiff hairs. Texture of lower surface: Glabrous except for dense pubescence along veins. Leaf length: Approximately 3.7 cm. Leaf width: Approximately 2.6 cm at widest point. Venation pattern: Pinnate. Color of upper surface of young foliage: Closest to 137A with venation of 145C. Color of lower surface of young foliage: 147B with venation of 145C. Color of upper surface of mature foliage: 146A with venation of 145B. Color of lower surface of mature foliage: 146B with venation of 145B. Petiole length: Approximately 8.2 mm. Petiole diameter: Approximately 1.7 mm. Petiole texture: Densely pubescent on both surfaces. Color of upper surface of petiole: 145B. Color of lower surface of petiole: 145C.

Flowering description:

*Flowering habit.*—'Balazwilro' is freely flowering under outdoor growing conditions with substantially continuous blooming from spring through autumn and year round in greenhouse environment.

*Inflorescence.*—Type: Corymb. Shape: Hemispherical to spherical. Quantity per plant: Approximately 5. Height: Approximately 3.7 cm. Width: Approximately 5.5 cm. Number of fully opened flowers per inflorescence at any one time: Approximately 18. Peduncle length: Approximately 4.6 cm. Peduncle diameter: Approximately 1.6 mm. Peduncle texture: Densely glandular pubescent. Peduncle color: Closest to 144A with glands of 183C.

*Lastingness of bloom.*—Approximately 5–7 days.

Flower description:

*Bud.*—Rate of opening: Generally takes 3–6 days for buds to progress from first color to fully open florets. Shape: Spherical to oval. Length: Approximately 4.9 mm. Diameter: Approximately 5.0 mm. Color: N66A.

*Flower.*—Type: Single, salverform, sessile. Fragrance: None detected. Corolla shape: Round. Corolla diameter: Approximately 2.2 cm.

*Petals.*—Quantity: Five, somewhat overlapping, fused at base to form tube. Shape: Obovate. Aspect: Slightly cupped. Appearance: Velvety. Margin: Entire. Apex: Emarginate. Texture: Color of upper surface when first open: Darker than N66A. Color of upper surface when fully open: N66A with 155C at base forming "eye". Color of lower surface when fully open: 61C at margin and center and 155C at base. Color of upper surface fades to 53C at senescence. Whiskers of 2D surround the opening of the corolla tube.

*Corolla tube.*—Length: Approximately 1.9 cm. Diameter at apex: Approximately 2 mm. Diameter at base: Approximately 1.3 mm. Texture: Pubescent on both surfaces. Color of both surfaces: 155A.

*Calyx.*—Shape: Tubular, 5 toothed, 5 ribbed formed by 5 fused sepals with stipule at base. Length: Approximately 1.2 cm. Diameter at apex: Approximately 3.2 mm. Diameter at base: Approximately 1.6 mm. Texture: Pubescent on both inner/upper and outer/lower surfaces. Color of inner/upper surface: 143D. Color of outer/lower surface: 143C. Stipule shape: Lanceolate. Stipule apex: Acute. Stipule base: Truncate. Stipule margin: Entire. Stipule length: 6 mm. Stipule width at base: 2 mm. Stipule color: 143B. Stipule texture: Long hairs, some with glands, on lower surface and along margin and short hairs on lower surface. Gland color: Colorless and transparent.

*Reproductive organs.*—There are 4 stamens. Anther shape: Bilobed, spade shaped Anther length: Approximately 1.1 mm. Anther color: 1A. Pollen amount: Moderate. Pollen color: 10D. Pistil quantity: 1. Pistil length: 1.9 cm. Stigma shape: Funnel. Stigma length: 0.9 mm. Stigma color: 144B. Style length: Approximately 1.6 cm. Style color: 145C. Ovary diameter: 2.3 mm. Ovary color: 144B.

Seed and fruit production: Neither seed nor fruit production has been observed.

Disease and pest resistance: Resistance to pests and pathogens common to *verbena* has not been observed.

What is claimed is:

1. A new and distinct cultivar of *Verbena hybrida* plant named 'Balazwilro', substantially as herein shown and described.

* * * * *